(12) United States Patent  (10) Patent No.: US 8,433,154 B2
Sehnert  (45) Date of Patent: Apr. 30, 2013

(54) ENHANCED CONTRAST FOR SCATTER COMPENSATION IN X-RAY IMAGING

(75) Inventor: William J. Sehnert, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 225 days.

(21) Appl. No.: 12/966,170

(22) Filed: Dec. 13, 2010

(65) Prior Publication Data

US 2012/0148156 A1    Jun. 14, 2012

(51) Int. Cl.
*G06K 9/40*    (2006.01)
*G06K 9/00*    (2006.01)

(52) U.S. Cl.
USPC .................................. 382/274; 382/132

(58) Field of Classification Search ........ 382/128–134, 382/168, 171, 173, 254, 274, 275, 305, 312; 345/617; 378/7, 21, 62; 424/9.3; 250/205; 600/410
See application file for complete search history.

(56) References Cited

U.S. PATENT DOCUMENTS

| | | | |
|---|---|---|---|
| 4,293,640 A * | 10/1981 | Weinberg | 430/421 |
| 4,814,597 A * | 3/1989 | Kruger et al. | 250/205 |
| 4,918,713 A | 4/1990 | Honda | |
| 5,440,647 A | 8/1995 | Floyd, Jr. et al. | |
| 5,615,279 A | 3/1997 | Yoshioka et al. | |
| 5,644,649 A * | 7/1997 | Schoeters et al. | 382/132 |
| 5,661,818 A | 8/1997 | Gaborski et al. | |
| 6,104,777 A | 8/2000 | Darboux et al. | |
| 6,269,176 B1 | 7/2001 | Barski et al. | |
| 6,459,765 B1 * | 10/2002 | Ganin et al. | 378/108 |
| 6,633,626 B2 | 10/2003 | Trotter et al. | |
| 6,768,784 B1 * | 7/2004 | Green et al. | 378/62 |
| 6,795,521 B2 | 9/2004 | Hsu et al. | |
| 6,923,950 B2 * | 8/2005 | Salb | 424/9.1 |
| 7,054,473 B1 | 5/2006 | Roehrig et al. | |
| 7,174,038 B2 | 2/2007 | Belykh et al. | |
| 7,218,702 B2 * | 5/2007 | Mistretta et al. | 378/21 |
| 7,522,756 B2 * | 4/2009 | Bueno et al. | 382/132 |
| 7,551,716 B2 | 6/2009 | Ruhrnschopf | |
| 7,756,316 B2 | 7/2010 | Odry et al. | |
| 8,089,278 B1 * | 1/2012 | Du | 324/307 |
| 8,150,126 B2 * | 4/2012 | Chen et al. | 382/130 |

* cited by examiner

*Primary Examiner* — Kanjibhai Patel (57) ABSTRACT

A method for rendering a radiographic image of a subject. Image data is obtained from an image detector and a look-up table is generated for image data processing, wherein the look-up table is generated at least according to information about an image type, an image detector type, and a kVp setting used to expose the radiographic image and according to information about grid use. Image data values of the obtained image data are adjusted according to the generated look-up table to generate adjusted radiographic image data. Log conversion and image processing are applied to the adjusted radiographic image data to form enhanced radiographic image data. The enhanced radiographic image data are rendered on a display.

20 Claims, 9 Drawing Sheets

ENHANCED CONTRAST FOR SCATTER COMPENSATION IN X-RAY IMAGING

FIELD OF THE INVENTION

The invention relates generally to the field of radiographic imaging and more particularly to methods for compensating for image scatter in X-ray images.

BACKGROUND OF THE INVENTION

The X-ray image that is formed from exposure of a patient or other subject to an X-ray beam has both primary and secondary components. The primary component is obtained from attenuation of the X-ray beam as it is absorbed by tissue or other materials along the beam path. The secondary component includes scattered radiation, where radiation energy is redirected in the tissue or other materials under examination rather than absorbed. Scattered energy is a type of unwanted signal or "noise" in the image and tends to blur and obscure the image, reducing image contrast.

Figure 1:
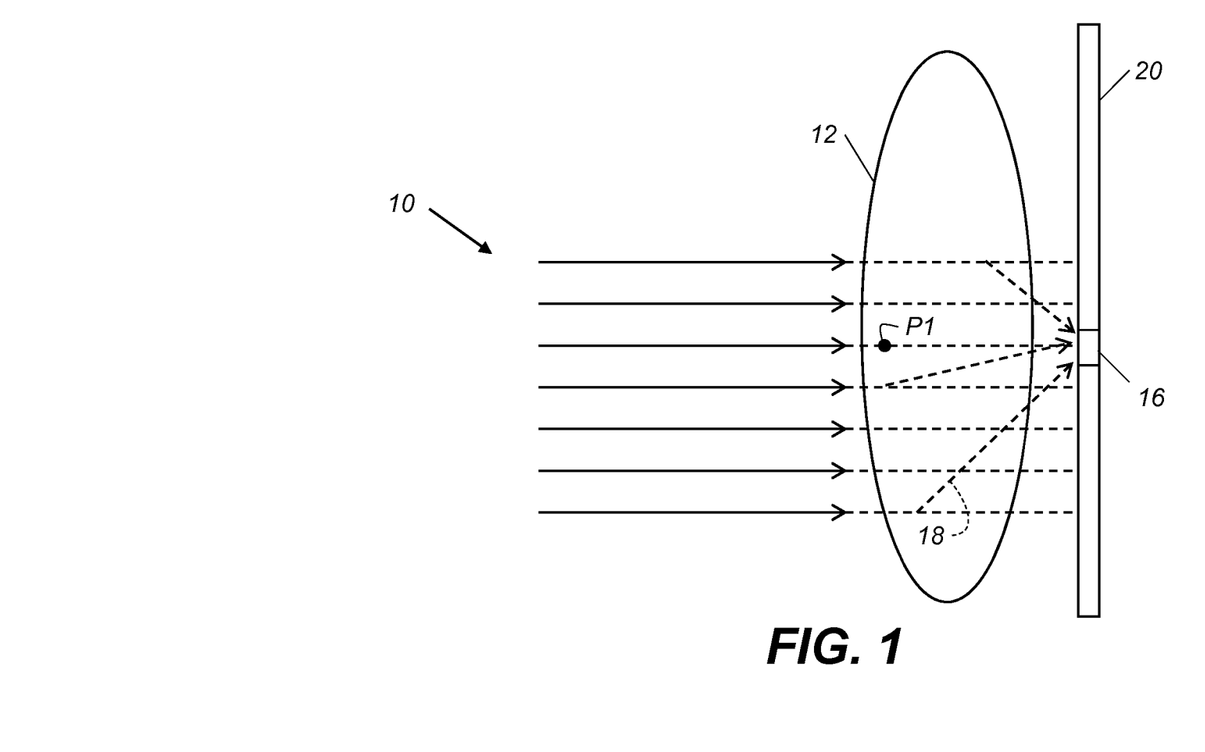
FIG. 1 is a schematic diagram that shows how scatter occurs in radiographic imaging.

The schematic diagram of FIG. 1 shows how scattered energy affects image content. Incident X-ray beams 10 are directed through a subject 12 and onto a detector 20. Detector 20 can be any of a number of types of X-ray image detector, such as a detector using a photosensitive film, a storage phosphor, or a digital sensor, as represented in FIG. 1. A pixel element 16 is shown for reference. The primary image content is obtained from attenuation of X-ray beams 10, traveling in a straight line, without redirection of the incident radiation energy. Information from absorption along a line through a point P1 is then obtained at pixel element 16, corresponding to point P1 of subject 12 as desired.

In the radiation scheme of FIG. 1, secondary image information is scattered energy that is not directed from a point within the subject to the nearest pixel element, as shown at a redirected beam 18. As the path of beam 18 shows, this type of scattered energy contributes to unwanted signal; in the case of FIG. 1, this redirected energy contributes to the signal at pixel element 16. The net effect of this redirected energy on the image is thus to add unwanted signal to the image, reducing image contrast and therefore adversely impacting image quality.

Scatter is typically quantified in terms of a Scatter-to-Primary ratio (S/P) wherein S indicates the amount of X-ray signal reaching the detector as a result of scatter of the primary beam and P represents the attenuated primary beam that reaches the detector in straight-line fashion, as shown in FIG. 1.

In some types of X-ray imaging, the percentage of scattered radiation expressed by S/P can be quite high, depending on various factors such as the radiation energy level applied, the subject's width, and content characteristics. For thicker body parts, such as the sub-diaphragm area in a chest exam, for example, the S/P ratio can be as high as 20:1 without a grid. Even within the relatively radio-lucent lung region, the S/P ratio may be on the order of 2:1 without a grid.

In the typical clinical imaging situation, one common method of reducing scatter is to use a radiographic grid. The grid uses a pattern of alternating radio-opaque (lead foil) and radiolucent (for example, aluminum) strips, arranged on edge to admit radiation between the strips. The edge of these strips is turned towards the x-ray source. The spacing of the strips determines the grid frequency, and the height-to-distance between lead strips determines the grid ratio. Grids can be oriented horizontally or vertically relative to the imaging medium. In a focused grid, the strips are angled to match the divergence of the x-ray beam. This arrangement helps to optimize the radiation path for the primary image content and to reduce scatter. Both stationary and moving grids can be used.

While the use of a grid can improve image contrast, there can be drawbacks to grid use. One drawback is the need to increase the dose when the grid is deployed. Other difficulties relate to practical concerns, including the need to position the grid, which may be awkward for the patient or technician, time-critical imaging requirements that may preclude taking the extra steps for grid positioning, system setup and use, and lack of standards for grid use. Different grid frequencies and grid ratios are optimized for different types of imaging conditions, complicating the job of specifying and locating the grid that might work best for a given examination. Another drawback is the potential for grid artifacts, such as shadows and aliasing, and the need for additional processing to suppress these artifacts in some cases.

In some hospital environments, the use of a grid for chest X-rays can be a standard or recommended practice. However, it can be difficult to enforce compliance and there can be urgent situations in which standard practices can be suspended. Moreover, even when a grid is used, some amount of scattering occurs. Thus, there is still a need for approaches that address the problem of scattering and compensate for scatter without compromising the image content.

There have been a number of approaches proposed for compensating for scatter in radiographic images using computational tools.

U.S. Pat. No. 6,104,777 entitled "Process for the Correction of Scattering in Digital X-Ray Images" to Darboux et al. describes an analytical approach that employs a 3-D model of the subject to estimate primary and secondary (scattered) image content. The method computes the scattered component using an integral transformation, then subtracts the secondary image content from the image.

U.S. Pat. No. 7,551,716 entitled "Apparatus and Method for Scatter Correction in Projection Radiography" to Ruhmschopf, primarily directed to mammography, employs a set of predefined tables, generated using Monte-Carlo simulation, that characterize the spread function of the scatter component in a scatter correction scheme.

U.S. Pat. No. 4,918,713 entitled "System and Method for Correcting for Scattered X-Rays" to Honda employs a characterization of the point spread function caused by scatter, then uses frequency transformation and convolution to identity and reduce the scatter component.

U.S. Pat. No. 6,633,626 entitled "Methods and Apparatus for Correcting Scatter" to Trotter et al. uses an iterative processing method to provide a variable scatter compensation based, in part, on the thickness of subject tissue.

U.S. Pat. No. 5,440,647 entitled "X-ray Procedure for Removing Scattered Radiation and Enhancing Signal-to-Noise Ratio (SNR)" to Floyd, Jr. et al. describes the use of a statistical estimation technique and an iterative algorithm that progressively removes image content that is due to scatter effects.

U.S. Pat. No. 5,615,279 entitled "Method of and Apparatus for Correcting Scattered X-rays for X-ray Computerized Tomograph" to Yoshioka et al. describes scatter correction using modeled data.

Approaches described in these disclosures include computational complexity and the need for substantial computer resources. This is a particular problem in urgent cases, where there may not be sufficient time for execution of full-blown image processing for scatter correction as taught in a number of the approaches listed previously. A further shortcoming of these solutions relates to the need for contrast uniformity, including providing some measure of consistent rendering for similar images, whether or not a radiographic grid is employed.

Thus, it can be seen that there is a need for scatter compensation that does not require extensive computer time and resources and that provides an improved measure of consistent rendering for presenting radiographic images.

SUMMARY OF THE INVENTION

An object of the present invention is to address the need for scatter compensation in radiographic images. With this object in mind, the present invention provides a method for rendering a radiographic image of a subject, the method executed at least in part on a computer and comprising: obtaining image data from an image detector; generating a look-up table for image data processing, wherein the look-up table is generated at least according to information about an image type, an image detector type, and a kVp setting used to expose the radiographic image and according to information about grid use; adjusting image data values of the obtained image data according to the generated look-up table to generate adjusted radiographic image data; applying log conversion and image processing to the adjusted radiographic image data to form enhanced radiographic image data; and rendering the enhanced radiographic image data on a display.

According to another aspect of the present invention there is provided a method for rendering a radiographic image of a subject, the method executed at least in part on a computer and comprising: obtaining image data from an image detector; segmenting the image data to identify one or more regions of interest in the radiographic image; generating a histogram of code values within each of the one or more regions of interest; obtaining a region representative value for each of the one or more regions of interest according to values in the generated histogram; generating a look-up table for contrast enhancement according to characterized image scatter within the radiographic image and according to one or more of the region representative values; applying the generated look-up table to the radiographic image to form enhanced radiographic image data; and rendering the enhanced radiographic image data on a display.

A feature of the present invention is its use of information about parameters under which the diagnostic image is obtained for compensating for scatter and providing improved rendering consistency.

An advantage of the present invention is its relative simplicity of implementation and relatively low computational resource requirements when compared against conventional methods for scatter correction.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

The following is a detailed description of the preferred embodiments of the invention, reference being made to the drawings in which the same reference numerals identify the same elements of structure in each of the several figures.

Where they are used, the terms "first", "second", and so on, do not necessarily denote any ordinal or priority relation, but may simply be used to more clearly distinguish one element from another.

The method of the present invention executes on a computer or other type of control logic processor, which may include a dedicated microprocessor or similar device. A computer program product used in an embodiment of the present invention may include one or more storage media, for example: magnetic storage media such as magnetic disk or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

Embodiments of the present invention use digital image data for an X-ray image, such as a chest X-ray image. The image data can be obtained from any of a number of types of image recording media, such as from a Digital Radiography (DR) detector that generates digital image data directly from received radiation; or from a Computed Radiography (CR) detector that stores energy from the radiation and is scanned in order to generate the digital image data; or from a film scanner that acts as a part of an image detector and scans developed X-ray film to generate digital image data therefrom.

By comparison with conventional methods for scatter compensation that can be highly computation-intensive and time-consuming, embodiments of the present invention do not attempt to suppress image scatter directly, such as by estimating and subtracting scatter content from the raw image data. Instead, the approach used in embodiments of the present invention is to enhance the image contrast in a way that suitably reduces the effects of scatter. The contrast enhancement techniques that are used also allow improved consistency of radiographic images, so that images obtained using different image recording media or that are obtained with different grids, or obtained without use of a grid, are rendered to have a similar appearance.

Figure 2:
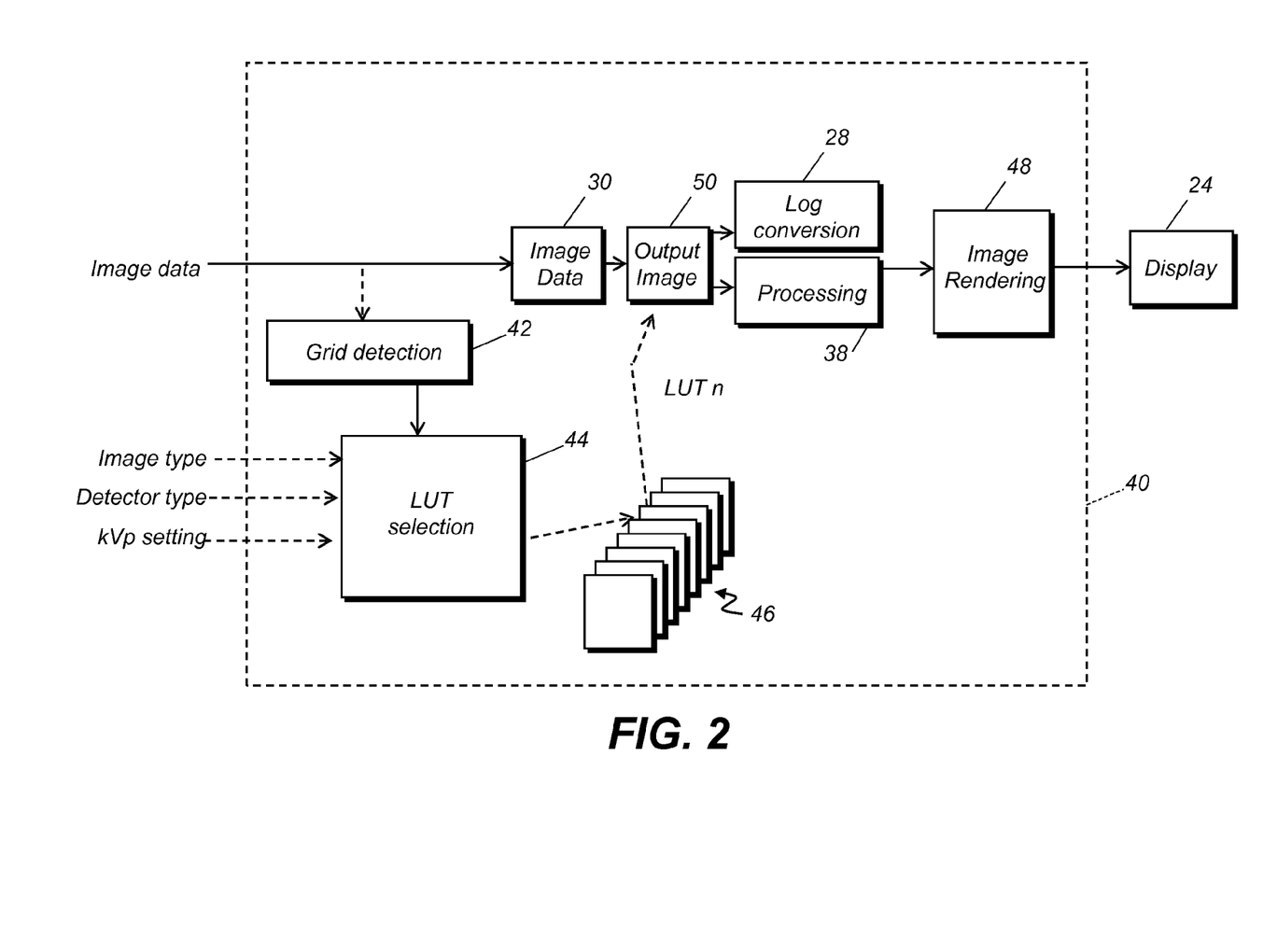
FIG. 2 is a schematic block diagram that shows the data flow and processing operations for rendering image data according to an embodiment of the present invention.

The data flow diagram of FIG. 2 shows how the method of the present invention operates upon the image data in order to generate an output image and compensate for scatter for viewing and archival in one embodiment. A processor 40, indicated by a dashed line in FIG. 2, performs the needed processing for generating an output image 50 from image data 30. For image rendering, processor 40 stores a number of look-up tables (LUTs) 46. A LUT selection process 44 selects a single LUT 46 from the stored set of LUTs and provides it to an image rendering process 48 for generating output image 50. There can be a number of criteria for LUT 46 selection, including the following:

(i) Image type. For the description that follows, the example of a chest X-ray image type is used. However, the method of the present invention can be used similarly for reducing scatter and providing more consistent rendering with other types of X-ray images.

(ii) Grid use. As was noted previously, the amount of scatter within an image and image data overall for the same subject can vary significantly depending on whether or not a grid was used. More detailed information is optional and can also be useful, such as frequency and height ratio information for a grid, where used.

(iii) Detector type. As is well known, the image data varies according to the type of image recording media that receives the radiation and on the circuitry that converts the received energy to digital data form. The range of values obtained from a digital DR detector, for example, exceeds the range of values that can be obtained from scanned film.

(iv) kVp setting. The amount of scatter varies with the kVp (kilovolt peak) setting; scatter increases with increased power. It is thus useful to identify a kVp setting or range of settings for scatter compensation.

A number of these criteria can be obtained from the imaging system itself. Image type (i), detector type (iii) and kVp setting (iv) are typically entered, recorded, and available from the X-ray console itself. Optionally, grid information (ii) may be obtained from the system. However, this requires an operator procedure to correctly enter information and parameters related to grid use, which may or may not be executed.

In the process flow of FIG. 2, a grid detection process 42 operates upon the image data itself in order to determine whether or not a grid was used. Grid detection algorithms are familiar to those skilled in the art. Exemplary grid detection methods are described in commonly assigned U.S. Pat. No. 6,269,176 entitled "Method for X-ray Antiscatter Grid Detection and Suppression in Digital Radiography" to Barski et al. and U.S. Pat. No. 7,174,038 entitled "Method for Antiscatter Stationary Grid Artifacts Detection and Attenuation in Digital Radiographic Images" to Belykh et al.

In addition to criteria (i)-(iv) listed previously, other differences that can condition LUT selection process 44 can include grid variables, such as grid frequency and height ratio. Thus, for example, a different LUT could be used where all other imaging conditions are the same, but only the grid frequency differs. Other operational variables available from the X-ray operator console or other source could optionally be used. Processing using LUT 46 then forms adjusted radiographic image data 50. A log conversion 28 and image processing 38 are then typically applied in order to form suitable enhanced image data for rendering in an image rendering process 48 as output image on a display 24.

Figure 3:
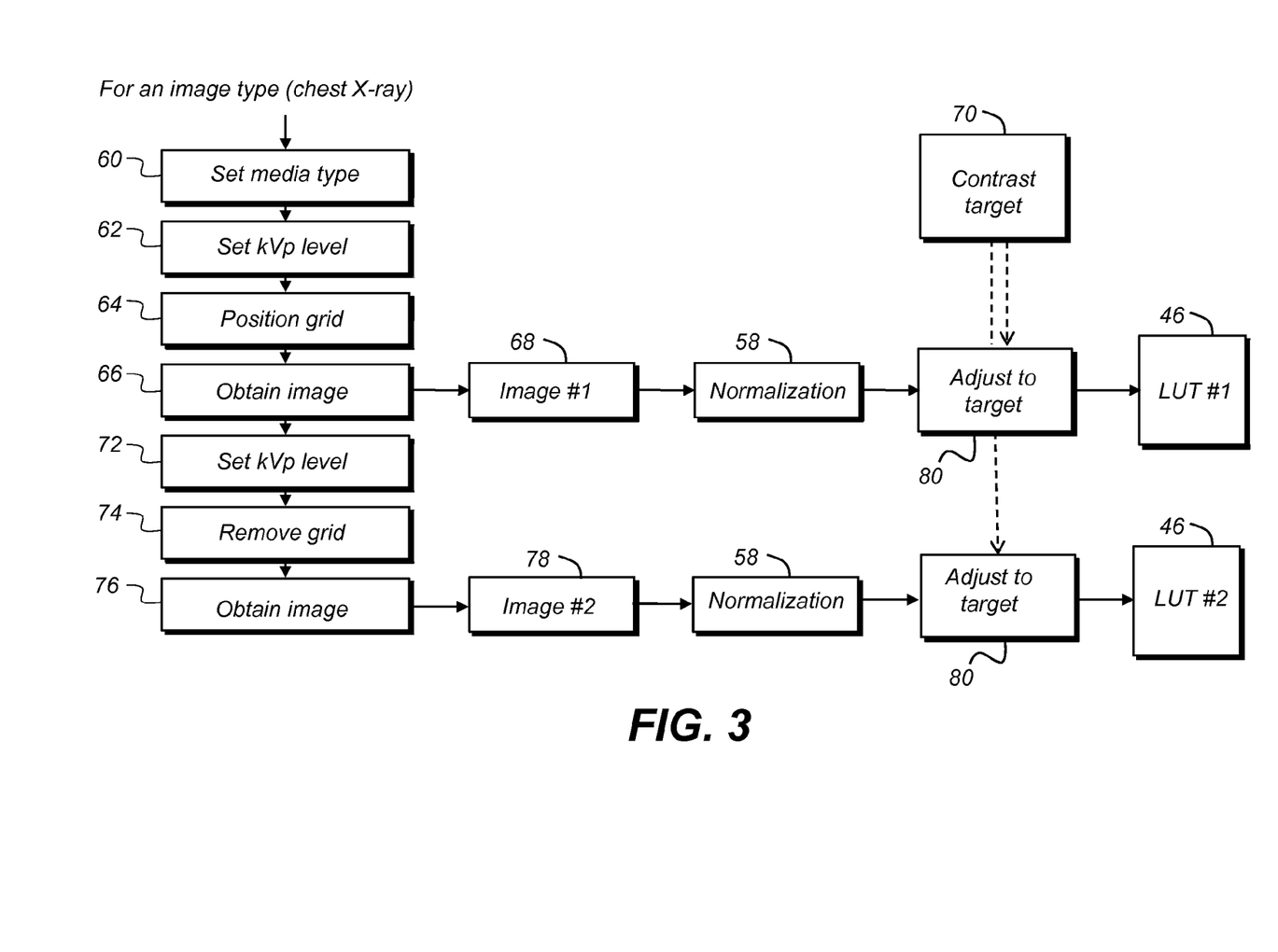
FIG. 3 is a schematic block diagram that shows the data flow and processing operations used for forming look-up tables in one embodiment.

As shown in the FIG. 2 embodiment, processor 40 selects one from a number of previously generated LUTs 46 based on criteria (i)-(iv). The process flow diagram of FIG. 3 shows how LUTs 46 are generated using a computer, workstation, or other type of logic processor in one embodiment. A phantom or other standard type of test image is used as the image type for generating LUTs in this example. In a set media type step 60, the recording media type is specified as either DR, CR, or scanned film. Following this, a first series of steps generates an interim image 68 for given conditions. A set power level step 62 sets up the kVp level for the upcoming exposure. In a grid position step 64, the operator places the grid in place for imaging. An image capture step 66 follows, exposing the phantom device and obtaining an interim image 68. With reference to the criteria for LUT application described earlier, interim image 68 data has associated image type (i), grid use information (ii), detector type (iii), and kVp setting (iv). An optional normalization step 58 is provided in order to adjust the exposure level for different detector types.

The process for obtaining an interim image 78 without the grid is similar using the process of FIG. 3. A set power level step 72 sets up the kVp level for the upcoming exposure. In a grid position step 74, the operator removes the grid for imaging. An image capture step 76 follows, exposing the phantom device and obtaining interim image 78. With reference to the criteria for LUT application described earlier, interim image 78 data similarly has associated image type (i), grid use information (ii), detector type (iii), and kVp setting (iv). Optional normalization step 58 is provided in order to adjust the exposure level for different detector types.

Continuing with the steps shown in FIG. 3, a contrast target 70 is used as a guide to remapping image data values in a mapping step 80 for each of interim images 68 and 78. Contrast target 70 specifies a range of image data values that provide enhanced contrast over the original image data. As a result of the processing shown in FIG. 3, two LUTs 46 are formed, each indexed by its corresponding criteria (i)-(iv). LUTs 46 can be stored as part of a library of LUTs and can be accessed as needed by processor 40, as was described earlier with reference to FIG. 2. The process described with reference to FIG. 3 can be repeated as many times as needed in order to generate and update the stored LUTs.

It is instructive to note that LUT generation can be an iterative process and that LUTs used at a particular site could be improved over time to better suit the imaging conditions and viewer preferences at an imaging site. For example, an individual LUT 46 may be initially configured to serve over a range of kVp values. Over time, it may be beneficial to generate additional LUTs, each better suited to a smaller range of values. Machine learning tools could also be applied to adapt existing LUTs based on viewer response to processor 40 over time. Techniques and methods for machine learning are familiar to those skilled in the imaging analysis arts.

Figure 4:
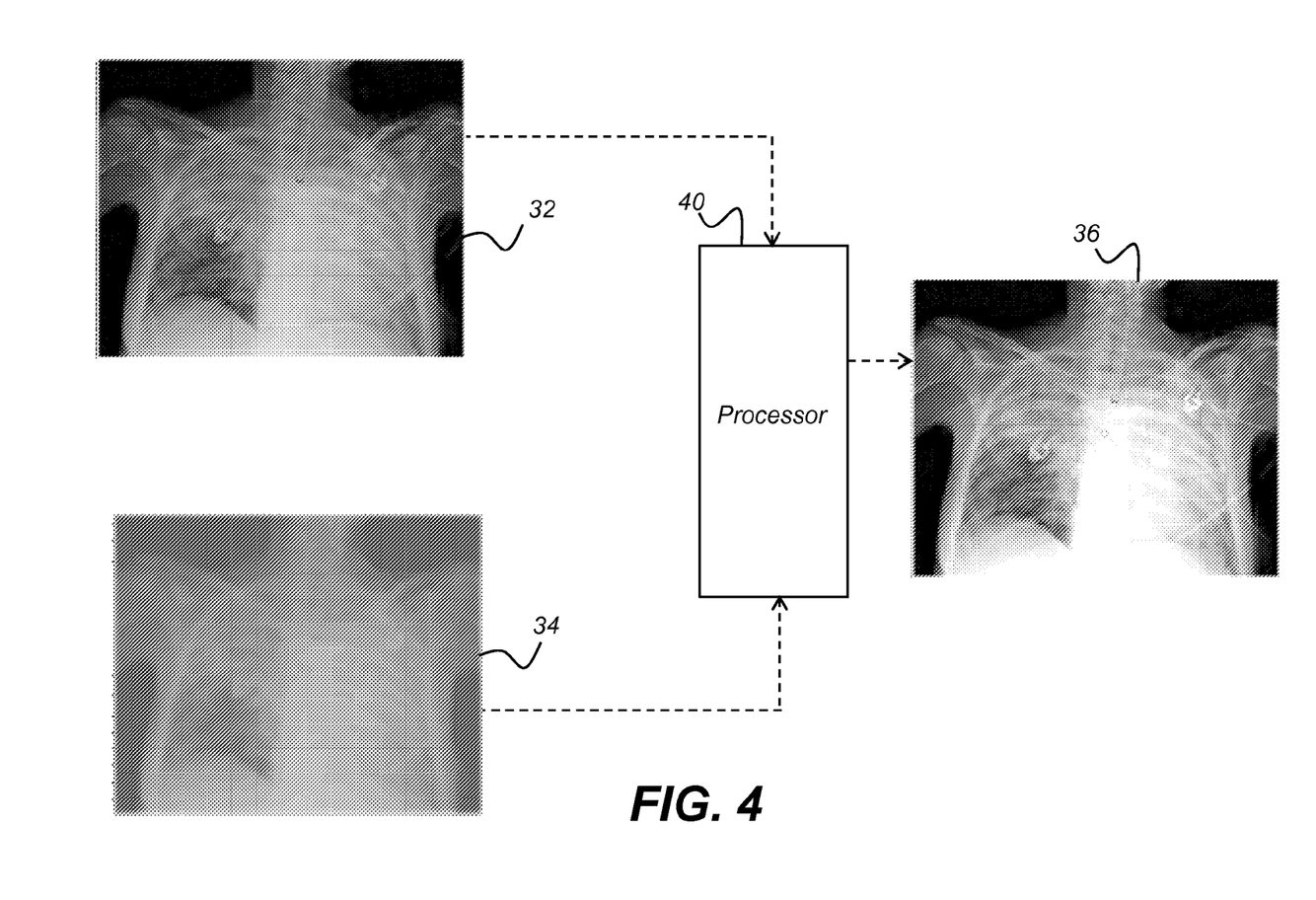
FIG. 4 is a schematic diagram that shows the use of the process of the present invention for rendering an image.

In addition to scatter compensation, adjustment of data values to contrast target 70 helps to provide consistency in rendering image data for the same image type where different recording media and power levels are used and whether or not a grid has been used. As shown in FIG. 4, an image 32 obtained using a grid has improved contrast over an image 34 obtained without grid use. Due, in part, to scatter, image 34 obtained without a grid, because it is typically generated at a lower kVp value than when a grid is used, can have a different range of values so that it has a different appearance for the same imaged subject. Processor 40, as was described in FIG. 2, can remap image data for both images 32 and 34 as described herein in order to improve contrast, diminish scatter appearance, and provide a more consistent output image 36.

Figure 5:
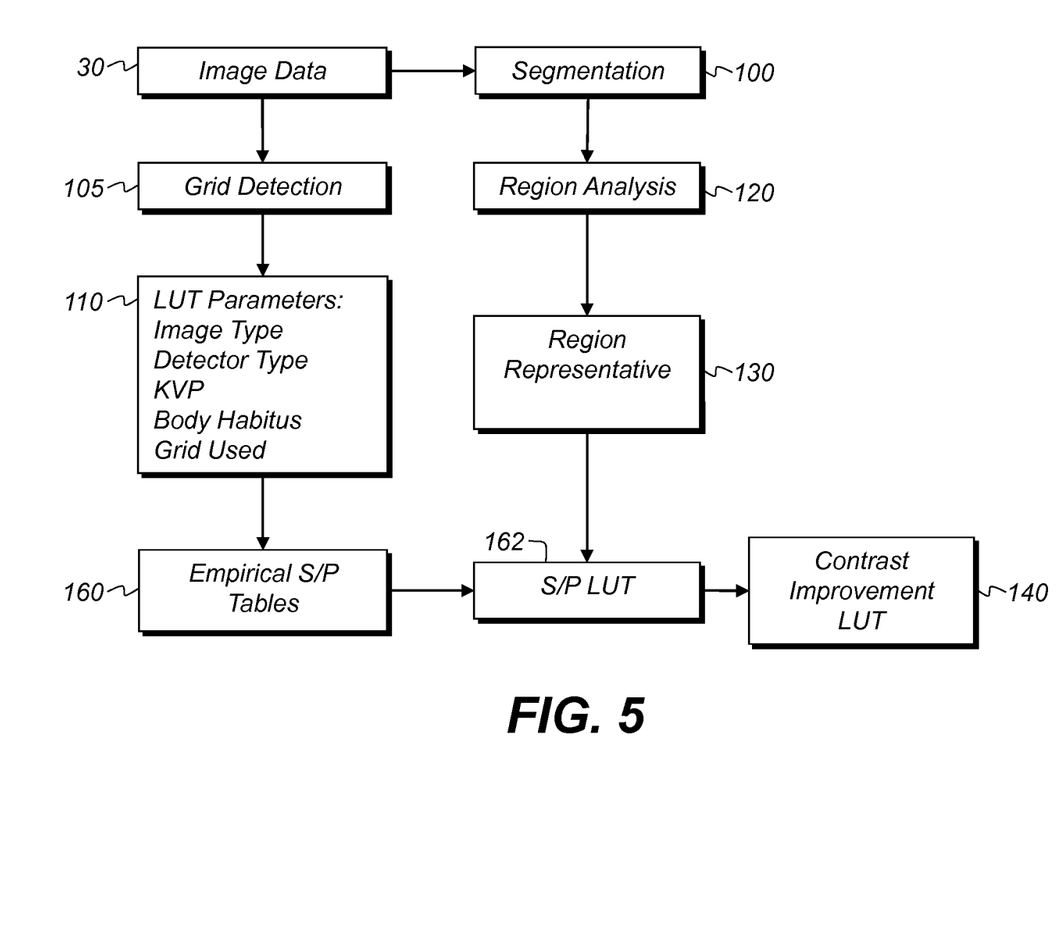
FIG. 5 is a logic flow diagram that shows generation of a look-up table using the image itself.

The embodiment described with reference to FIG. 2 set up and used a set of LUTs that could be indexed and applied according to various criteria about the image type and imaging characteristics. In a related approach, alternate embodiments of the present invention also set up and use an LUT that is generated on a per-image basis, using empirically obtained information on S/P characteristics but depending heavily on data values from within the image itself. The data flow diagram of FIG. 5 shows how an embodiment of the present invention does this, operating upon the input image data to compensate for scatter and thereby generating image data that has enhanced contrast. For clarity of description, the steps of this sequence are described with reference to a 16-bit chest x-ray image as an example, wherein the digital code values provided are substantially linear with respect to exposure.

Referring to the sequence of FIG. 5, image data 30 is first input to a grid detection process 105 in order to determine whether or not a grid was used in image acquisition. This data and other information related to image acquisition are stored in memory as image parameters acquisition 110. These parameters may include, but are not limited to, the x-ray energy, kVp value, the type of imaging detector used, the type of grid used for acquisition (including the case where no grid was used), the body part imaged, and patient body habitus, for example. A number of these parameters may be useful for improving accuracy, such as patient habitus or overall physique. However, such a parameter may not be needed in some cases. An empirical S/P table 160, previously generated from data obtained under the same or substantially the same imaging parameters, is then accessed to be used for LUT generation in subsequent processing.

Still referring to the sequence of FIG. 5, image data 30 is then input to a segmentation step 100, a process that segments the image into representative or significant regions of interest (ROIs). Segmentation processing uses techniques well known to those skilled in the imaging analysis arts. By way of example, segmentation processing for chest x-ray images is described in U.S. Pat. No. 6,795,521 entitled "Computer-Aided Diagnosis System for Thoracic Computer Tomography Images" to Hsu et al. and in U.S. Pat. No. 7,756,316 entitled "Method and System for Automatic Lung Segmentation" to Odry et al.

Figure 6:
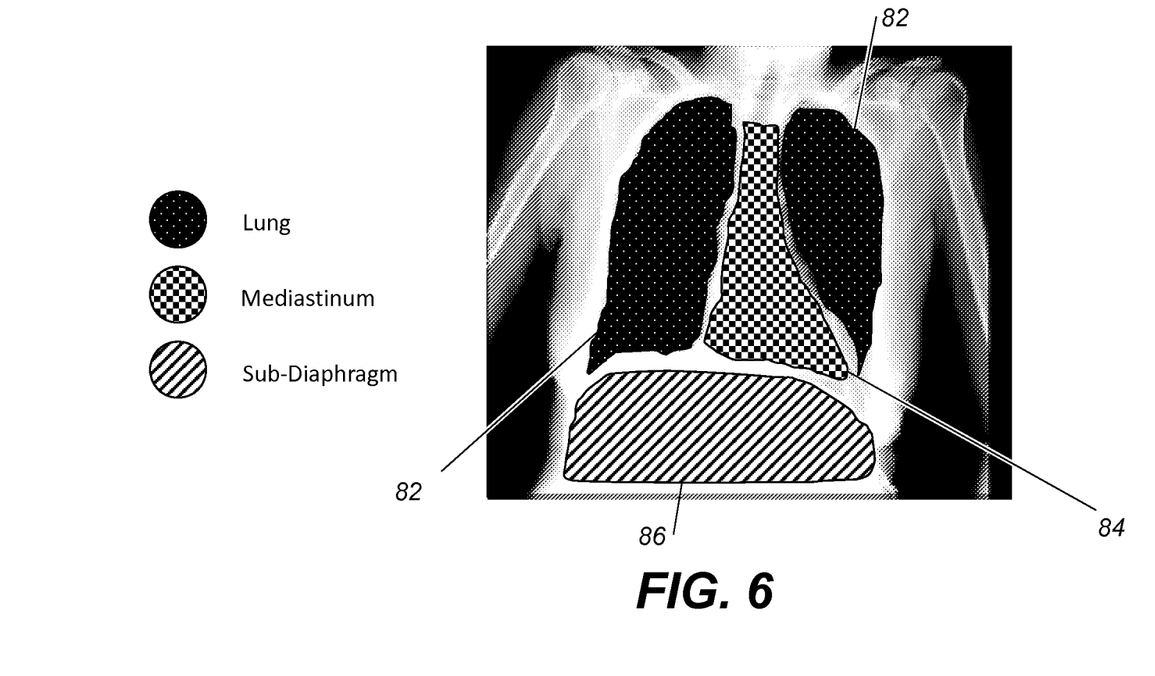
FIG. 6 is a plan view showing primary regions of a chest x-ray for segmentation.

The plan view of FIG. 6 shows the primary regions of interest detected within a chest x-ray image, namely lung fields 82, mediastinum 84, and sub-diaphragm region 86. Referring back to the sequence of FIG. 5, a region analysis step 120 is executed following this segmentation process. In region analysis step 120, these regions of interest are individually analyzed to determine a representative digital code value for each region. This value serves as its region representative 130. In one embodiment of the invention, region representative 130 is a code value chosen by selecting the mode of the histogram that is formed from the code values of the pixels in the region. A statistical metric, the mode of a set of values is the value that is most often repeated. Alternate embodiments may use other statistical values, including the mean or median, for example, or some value derived from a combination of statistics obtained from the histogram.

Figure 7:
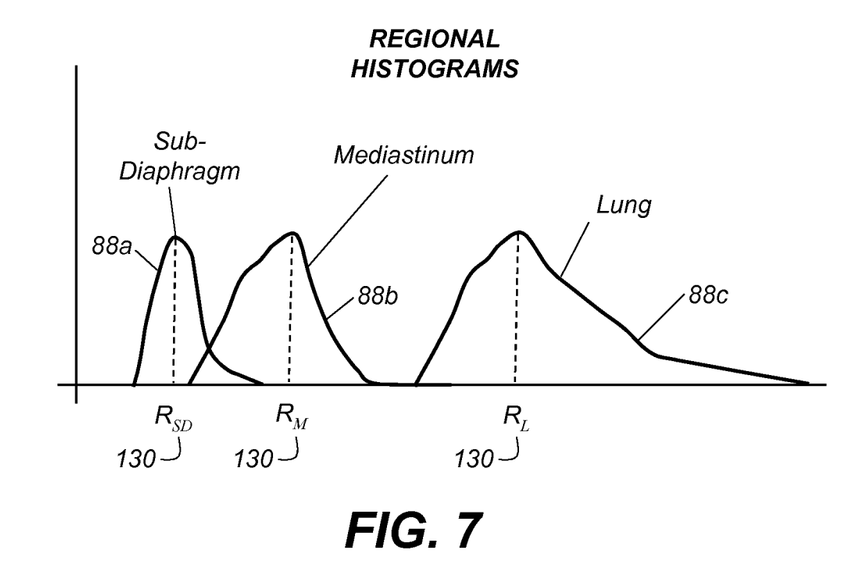
FIG. 7 is a graph showing regional histogram data for primary regions identified in FIG. 6.

The graph of FIG. 7 shows regional histograms 88a, 88b, and 88c for sub-diaphragm, mediastinum, and lung regions, respectively. For each region, the mode is used as region representative 130.

Figure 8:
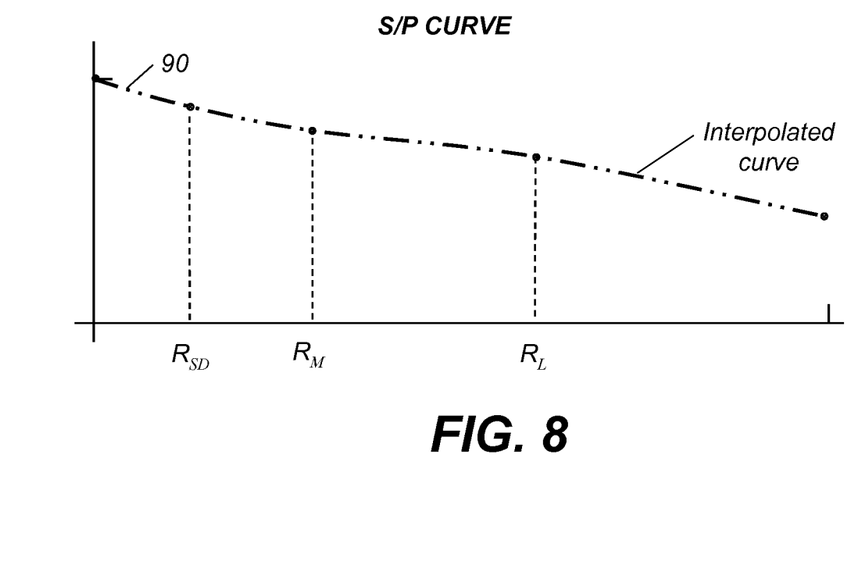
FIG. 8 is a graph showing a representative S/P curve for a chest x-ray.

FIG. 8 shows an intermediate S/P curve 90 that can then be generated for characterizing image scatter. Having segmented the image and determined the regional representatives 130 for the relevant regions of the image, an intermediate S/P curve is constructed from the region representatives 130 and the x-ray image acquisition information 110. Using S/P data from empirical tables 160, the S/P curve 90 is initialized with the three points ($R_{SD}$, $S/P_{RSD}$), ($R_M$, $S/P_{RM}$), and ($R_L$, $S/P_{RL}$) and then interpolated to accommodate the endpoints (0, 1.0) and, for a 16-bit image, (65535, $S/P_{Min}$) as shown in FIG. 8. The low-signal endpoint (0, 1.0) is only a theoretical limit of S/P as the detected signal approaches zero. The high-signal endpoint, furthest to the right in the graph of FIG. 8, comes from the empirical S/P table 160 based on acquisition information 110. The example in FIG. 8 is for an image that was acquired without the use of a grid, as is indicated by the relatively large values of the S/P components on the curve. The points are then interpolated in a manner that preserves the decreasing monotonicity dictated by the physical process. Referring back to the logic flow shown in FIG. 5, the S/P relationships represented in curve 90 are then used to generate an S/P LUT 162 in a manner familiar to those skilled in the image processing art.

Figure 9:
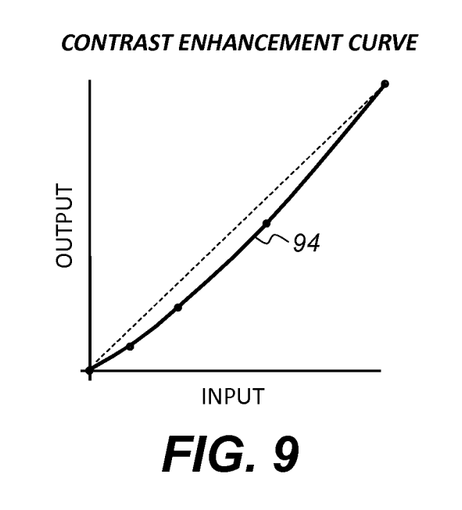
FIG. 9 is a graph that shows the function of a look-up table for contrast enhancement in one embodiment.

From intermediate SIP curve 90 and its corresponding S/P LUT 162, a contrast enhancement curve 94, as shown in FIG. 9 with a corresponding contrast improvement LUT 140 (FIG. 5), can be constructed as outlined in the following sequence. For a given pixel in the x-ray image, let n denote the 16-bit digital value that was output by the detector at that pixel location. The value n represents a quantity that is proportional to x-ray exposure—that amount detected at the given pixel location. Some of this exposure is due to the primary x-ray beam, another portion is due to scattered radiation. This relationship of scattered to primary exposure energy that can be used for image scatter characterization can be expressed as follows:

$$n = P(n) + S(n) \quad \text{(Eqn 1)}$$

The scatter part, S(n), of the exposure value n can be removed by applying the S/P curve. Indeed, using the simple relationship $$S(n) = S/P(n) \cdot P(n) \quad \text{(Eqn 2)}$$

allows solving for the primary component, P(n), as $$P(n) = n/(1 + S/P(n)) \quad \text{(Eqn 3)}$$

Equation (3) is applicable regardless the value of n and defines the relationships to form the contrast enhancement curve 94. This curve characteristic is used to generate contrast enhancement LUT 140. Although in this example contrast enhancement LUT 140 is generated in a digital space where code values are proportional to x-ray exposure, it should be noted that LUT 140 could alternately be generated in a digital space where code values are linearly related to the logarithm of exposure.

While the invention has been described with reference to exemplary embodiments for use with X-ray chest imaging, it will be understood by those skilled in the art that, for obtaining other types of images, various changes may be made and equivalents may be substituted for elements thereof without departing from the scope of the invention. In particular, a different set of LUTs would be generated for the type of image, detector type, and power levels, as well as for grid use. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A method for rendering a radiographic image of a subject, the method executed at least in part on a computer and comprising:
   accessing radiographic image data;
   generating a look-up table for image data processing, wherein the look-up table is generated at least according to information about an image type, an image detector type, and a kVp setting used to expose the radiographic image and according to information about grid use;
   adjusting image data values of the obtained image data according to the generated look-up table to generate adjusted radiographic image data;
   applying log conversion and image processing to the adjusted radiographic image data to form enhanced radiographic image data; and
   storing, transmitting, or displaying the enhanced radiographic image data.

2. The method of claim 1 wherein generating the lookup table further comprises obtaining a grid frequency.

3. The method of claim 1 wherein generating the lookup table is performed prior to obtaining the image data.

4. The method of claim 1 wherein generating the lookup table further comprises segmenting the image data to identify one or more regions of interest.

5. The method of claim 1 wherein generating the lookup table further comprises applying a normalization process to the image data.

6. The method of claim 1 wherein generating the lookup table further comprises making an adjustment according to a contrast target.

7. The method of claim 1 wherein generating the lookup table is repeated one or more times to form a set of lookup tables.

8. The method of claim 1 wherein displaying comprises rendering the enhanced radiographic image data on a display.

9. The method of claim 1 wherein the radiographic image data is obtained from an image detector.

10. The method of claim 9 wherein the image detector is taken from the group consisting of a digital radiography detector and a computed radiography detector.

11. The method of claim 9 wherein the image detector comprises a film scanner.

12. A method for rendering a radiographic image of a subject, the method executed at least in part on a computer and comprising:
    accessing radiographic image data;
    segmenting the image data to identify one or more regions of interest in the radiographic image;
    generating a histogram of code values within each of the one or more regions of interest;
    obtaining a region representative value for each of the one or more regions of interest according to values in the generated histogram;
    generating a look-up table for contrast enhancement according to characterized image scatter within the radiographic image and according to one or more of the region representative values;
    applying the generated look-up table to the radiographic image to form enhanced radiographic image data; and
    storing, transmitting, or displaying the enhanced radiographic image data.

13. The method of claim 12 wherein generating the lookup table further comprises obtaining a grid frequency.

14. The method of claim 12 wherein obtaining the region representative value comprises obtaining a mode value from the histogram.

15. The method of claim 12 wherein displaying comprises rendering the enhanced radiographic image data on a display.

16. The method of claim 12 wherein the radiographic image data is obtained from an image detector.

17. The method of claim 16 wherein the image detector is taken from the group consisting of a digital radiography detector, a computed radiography detector, and a film scanner.

18. A method for rendering a radiographic image of a subject, the method executed at least in part on a computer and comprising:
    accessing radiographic image data;
    segmenting the image data to identify one or more regions of interest in the radiographic image;
    generating a histogram of code values within each of the one or more regions of interest;
    obtaining a region representative value for each of the one or more regions of interest according to values in the generated histogram;
    generating a scattered to primary ratio relationship using the region representative values from each of the one or more regions of interest and using an image scatter characterization;
    generating a look-up table for contrast enhancement according to the generated scattered to primary ratio relationship;
    applying the generated look-up table to the radiographic image to form enhanced radiographic image data; and
    storing, transmitting, or displaying the enhanced radiographic image data.

19. The method of claim 18 wherein displaying comprises rendering the enhanced radiographic image data on a display.

20. The method of claim 18 wherein the radiographic image data is obtained from an image detector.

* * * * *